United States Patent
Kakimoto et al.

[11] Patent Number: 5,744,023
[45] Date of Patent: Apr. 28, 1998

[54] METHOD FOR SEPARATION AND RECOVERY OF ORGANOGERMANIUM COMPOUND

[75] Inventors: Norihiro Kakimoto, Tokyo; Keiji Umeda, Ibaraki; Takashi Ichimura, Chiba, all of Japan

[73] Assignees: Asai Germanium Research Institute Co., Ltd.; Asahi Glass Company, both of Tokyo, Japan

[21] Appl. No.: 602,842

[22] PCT Filed: Jun. 28, 1995

[86] PCT No.: PCT/JP95/01286

§ 371 Date: Feb. 27, 1996

§ 102(e) Date: Feb. 27, 1996

[87] PCT Pub. No.: WO96/00731

PCT Pub. Date: Jan. 11, 1996

[30] Foreign Application Priority Data

Jun. 28, 1994 [JP] Japan ................. 6-170136

[51] Int. Cl.⁶ ............... C13D 1/00; C13D 3/18
[52] U.S. Cl. ............ 205/697; 205/421; 205/703; 204/530; 204/544
[58] Field of Search .................. 205/421, 446, 205/457, 697, 702, 703; 204/522, 523, 530, 544; 436/239

[56] References Cited

U.S. PATENT DOCUMENTS

| | | | |
|---|---|---|---|
| 3,440,159 | 4/1969 | McRae et al. | 426/239 |
| 4,133,696 | 1/1979 | Barker et al. | 127/46 A |
| 4,299,677 | 11/1981 | Venkatasubramanian et al. | 204/180 P |
| 4,885,247 | 12/1989 | Datta | 204/530 |
| 5,464,514 | 11/1995 | Pluim et al. | 204/182.4 |

FOREIGN PATENT DOCUMENTS

| | | |
|---|---|---|
| 4-227822 A | 8/1992 | Japan . |
| 7-61989 A | 3/1995 | Japan . |
| 1497888 | 1/1978 | United Kingdom . |
| 94/14826 | 7/1994 | WIPO . |

*Primary Examiner*—Kathryn L. Gorgos
*Assistant Examiner*—Alex Noguerola
*Attorney, Agent, or Firm*—Kubovcik & Kubovcik

[57] ABSTRACT

An electric current is passed through a mixed solution containing a saccharide(s) and an organogermanium compound, in a compartment whose anode side is defined by an anion exchange membrane and whose cathode side is defined by a cation exchange membrane, to separate and remove said organogermanium compound. In the present invention, an organogermanium compound can be very effectively separated and recovered from a mixed solution containing a saccharide(s) and said organogermanium compound. The present invention is particularly effective for separation and recovery of an organogermanium compound from a reaction mixture obtained when a compound having an aldose structure is isomerized into a compound having a ketose structure in the presence of said organogermanium compound.

7 Claims, 1 Drawing Sheet

METHOD FOR SEPARATION AND RECOVERY OF ORGANOGERMANIUM COMPOUND

This application is a 371 of PCT/JP95/01286, filed Jun. 28, 1995, which is now WO96/00731.

TECHNICAL FIELD

The present invention relates to a method for separating and recovering an organogermanium compound from a mixed solution containing a saccharide(s) and the organogermanium compound. More particularly, the present invention relates to a method for separating and recovering an organogermanium compound from a mixed solution containing a saccharide(s) and the organogermanium compound, obtained when a compound having an aldose structure [e.g. glucose (grape sugar)] is isomerized into a compound having a ketose structure [e.g. fructose (fruit sugar)] in the presence of the organogermanium compound.

BACKGROUND ART

Carbohydrates, which are organic compounds very important to organisms as an energy source, etc. and present most abundantly on the earth, are basically composed mainly of monosaccharides. These monosaccharides each have a typical structure in which 3–8 carbon atoms are linked to form a ring, and the structure is largely classified into two kinds, i.e. an aldose (a saccharide having an aldehyde group) and a ketose (a saccharide having a ketone group). The aldose and the ketose are classified into respective trioses, tetroses, pentoses, hexoses, etc. depending upon the number of carbon atoms.

It is known that the monosaccharides are isomerized by various reactions to modify their structures and properties. Such isomerization includes, for example, isomerization of glucose (grape sugar) which is an aldohexose of low sweetness into corresponding fructose (fruit sugar) which is a ketohexose of high sweetness to produce an isomerized saccharose.

Isomerized saccharose is a mixture of fructose (fruit sugar) obtained by partial isomerization of glucose and unreacted glucose (grape sugar). Owing to the partial isomerization of glucose having low sweetness into fructose having high sweetness, isomerized saccharose has sweetness similar to that of sugar (sucrose). About 70% of the total isomerized saccharose consumption is used in refreshing drinks because fructose contained in isomerized saccharose has higher sweetness at lower temperatures, and the remainder is used in general foodstuffs.

Both glucose and fructose are hexoses having a similar chemical structure. Various processes have hitherto been proposed for isomerization of glucose into fructose. Isomerization of glucose into fructose is currently conducted in industry as follows. That is, starch, for example, corn starch is liquidized; the resulting liquid is subjected to saccharification using glucoamylase to obtain a saccharose solution; and passing the saccharose solution continuously through an immobilized enzyme obtained by immobilizing, using one of various methods, an isomerase produced by a microorganism of, for example, Streptomyces genus, to isomerize the glucose contained in said solution to fructose.

The above isomerization reaction is an equilibrium reaction whose equilibrium constant is 1 or thereabout (the reaction is faster at a higher temperature but the equilibrium constant does not change substantially). At the equilibrium state, about 50% of glucose can be isomerized into fructose at a reaction temperature of about 60° C. In order to allow the isomerization to proceed to such a level, however, a considerable length of time is required, the reaction mixture is colored owing to the heating for such a long time, and a high cost is incurred for the steps of purification and condensation which are necessary for product marketing. Hence, the reaction is terminated when the isomerization has proceeded to a fructose content of about 42%.

The thus-obtained isomerized saccharose containing fructose in an amount of about 42%, however, has a sweetness of about 95–100 when the sweetness of sucrose is taken as 100, and is slightly insufficient in sweetness. Therefore, subsequent concentration is necessary. The concentration, however, requires a large apparatus. Moreover, a complicated operation must be conducted; that is, a fructose solution containing about 95% of fructose is obtained using the large apparatus, and then the fructose solution is mixed with the 42% isomerized saccharose to obtain an isomerized saccharose having a sweetness of 100–110 (isomerization ratio=50%).

Isomerization of other compounds having an aldose structure into compounds having a ketose structure includes, for example, isomerization of lactose (a disaccharide) into lactulose. In this case, however, since no enzyme useful for isomerization of lactose into lactulose is found yet unlike the above case of glucose isomerization, the isomerization is conducted, for example, by adding sodium hydroxide to lactose in a desired concentration and heating the resulting mixture to a temperature of 70° C. or higher (Japanese Patent Publication No. 2984/1977).

With the above approach, however, the isomerization ratio of lactose, i.e. yield of lactulose, is low at 20% or less. In order to obtain a solution or syrup containing a lactulose in a high concentration, the lactulose solution must be concentrated.

The present inventors made a study from various angles, in view of the above-mentioned problems of the prior art. As a result, the present inventors previously discovered an interaction between saccharide and an organogermanium compound containing an organic acid or an amino acid as the basic skeleton and developed a process capable of directly producing an isomerized saccharose having a sweetness the same as or higher than that of sucrose, by isomerizing glucose into fructose at a high isomerization ratio using an isomerase, in the presence of an organogermanium compound. The present inventors have made a further study and previously developed and proposed a process for isomerizing a compound having an aldose structure into a compound having a ketose structure in the presence of an organogermanium compound in the presence or absence of an isomerase (i.e. regardless of the presence or absence of the isomerase) (Japanese Patent Application Nos. 360343/1992 and 188877/1993).

The above processes are characterized by isomerizing a compound having an aldose structure into a compound having a ketose structure in the presence of an organogermanium compound having a structural moiety represented by the following formula (1) and an organic group (e.g. a chain or cyclic type hydrocarbon or a substitution compound or derivative thereof) bonded thereto, in the presence or absence of an isomerase. The organogermanium compound is specifically an organogermanium compound represented by the following formula (2).

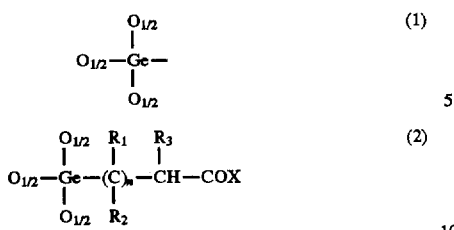

(1)

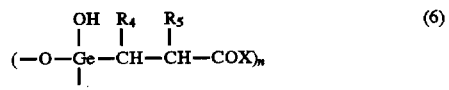

(6)

(wherein $R_4$ and $R_5$ may be the same or different and are each independently a hydrogen atom or a lower alkyl group; X is a hydroxyl group, a lower alkyl group or an O-lower alkyl group; and n is an integer of 1 or more).

[wherein $R_1$ to $R_3$ may be the same or different and are each independently a hydrogen atom, a lower alkyl group, a carboxyalkyl group, a substituted or unsubstituted phenyl group or an amino group which may be protected by an appropriate protective group; X is a hydroxyl group, an O-lower alkyl group, an amino group or a salt represented by OY (wherein Y is a metal or a basic compound); and n is an integer of 1 or more].

The organogermanium compound can be exemplified by a compound which has, as the basic skeleton, a germylpropionic acid formed by linkage of a germanium atom and a propionic acid derivative having three substituents $R_1$ to $R_3$ and an oxygen functional group OX and in which the germanium atom in the basic skeleton bonds to oxygen atoms at an atomic ratio of 2:3. The substituents $R_1$ and $R_2$ may be the same or different, are present at an α-or a further position relative to the germanium atom, and, when n is 1, 2, ..., n, become $R_{11}, R_{12}, ..., R_{1n}$ and $R_{21}, R_{22}, ..., R_{2n}$ and bond to a respective carbon chain represented by "—$(C)_n$—" (n is an integer of 1 or more). The substituent $R_3$ bonds to the methylene group between the carbon chain $(C)_n$ and the oxygen functional group.

The substituents $R_1$ to $R_3$ are each a hydrogen atom, a lower alkyl group (e.g. methyl, ethyl, propyl or butyl), a carboxyalkyl group, a substituted or unsubstituted phenyl group or an amino group. The substituent X is a hydroxyl group, an O-lower alkyl group, an amino group or a salt of a carboxylic acid represented by OY wherein Y is a monovalent or higher valent metal (e.g. sodium or potassium) or a basic compound typified by lysozyme or a basic amino acid (e.g. lysine).

The structure of the formula (2) representing the organogermanium compound is for the compound in a crystal state. The compound can be represented by the following formula (3) when it is dissolved in water. The compound always takes a structure of $(HO)_3Ge$ as shown in the formula (3), when dissolved in water. The compound can also be represented by the following formula (4).

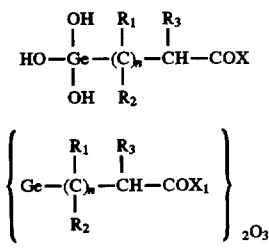

In the present invention, there can also be used those organogermanium compounds represented by the following formula (5) or (6), disclosed in, for example, Japanese Patent Application Kokai (Laid-Open) No. 18399/1984:

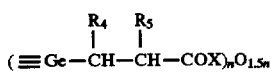

In the above-mentioned isomerization process proposed previously, a compound having an aldose structure is isomerized into a compound having a ketose structure in the presence of the above-mentioned organogermanium compound. In the isomerization process, the compound having an aldose structure to be isomerized includes, for example, monosaccharides and disaccharides shown in Table 1 as compounds (A) to be isomerized. They can be converted into corresponding isomerization products (B) of ketose structure. In the isomerization process, even oligosaccharides (trisaccharides and higher saccharides) of aldose structure can be isomerized.

TABLE 1

| | Compounds (A) to be isomerized | Isomerization products (B) |
|---|---|---|
| 1 | Glyceraldehyde | Dihydroxyacetone |
| 2 | Erythrose, threose | Erythrulose |
| 3 | Ribose, arabinose | Ribulose |
| 4 | Xylose, lyxose | Xylulose |
| 5 | Allose, altrose | Psicose |
| 6 | Glucose, mannose | Fructose |
| 7 | Gulose, idose | Sorbose |
| 8 | Galactose, talose | Tagatose |
| 9 | Maltose (reducing disaccharide) | Maltulose |
| 10 | Lactose (reducing disaccharide) | Lactulose |

All of the above-mentioned organogermanium compounds have very low toxicity [for example, a compound having the above formula (2) wherein n=1, $R_1$=$R_2$=$R_3$=H and X=OH (a compound having compound No.=1 in Table 2 shown below) gives a $LD_{50}$ of at least 6 g/kg in mice and a $LD_{50}$ of at least 10 g/kg in rats when orally administered to them] and have very high safety and excellent stability. Since these organogermanium compounds are an expensive and valuable resource, it is desirable that they can be separated and recovered from respective reaction mixtures for reutilization. However, both the saccharides and the organogermanium compounds are organic compounds of fairly high molecular weights and no method for effective separation of the two kinds of the compounds is known.

In view of the above situation, the present inventors made a study from various angles on a method for separating and recovering an organogermanium compound from a reaction mixture obtained when a compound having an aldose structure is isomerized to a compound having a ketose structure in the presence of said organogermanium compound used as an isomerization agent or an isomerization accelerator. As a result, the present inventors found out that the organogermanium compound can be separated and recovered very effectively by using ion exchange membranes. The finding has led to the completion of the present invention.

The present invention is intended to provide a method for very effectively separating and recovering an organogermanium compound, by using ion exchange membranes, from a reaction mixture obtained when a compound having a aldose structure is isomerized to a compound having a ketose structure in the presence of said organogermanium compound used as an isomerization agent or an isomerization accelerator.

SUMMARY OF THE INVENTION

The present invention provides a method for separating and recovering an organogermanium compound from a mixed solution containing a saccharide(s) and said organogermanium compound, which method comprises passing an electric current through a mixed solution containing a saccharide(s) and an organogermanium compound, in one or more compartments each defined by one pair of an anion exchange membrane and a cation exchange membrane facing each other, whose anode side is defined by an anion exchange membrane and whose cathode side is defined by a cation exchange membrane, to separate and recover said organogermanium compound from said mixed solution.

BEST MODE FOR CARRYING OUT THE INVENTION

Figure 1:
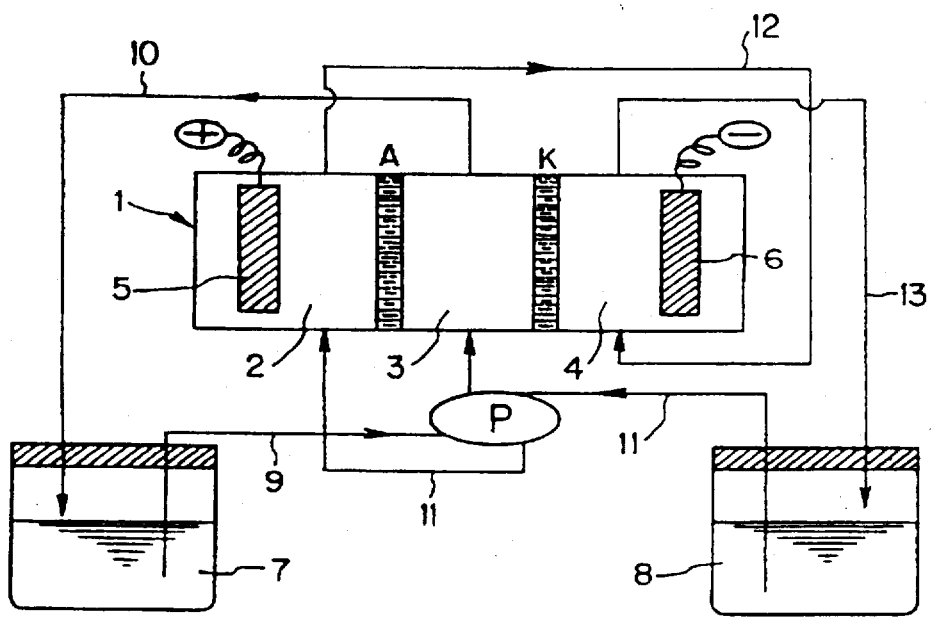
FIG. 1 is a schematic drawing showing the principle of an electrodialysis apparatus for carrying out the present invention method.

The present invention is hereinafter described in detail.

In the present invention, the saccharide(s) contained in the mixed solution can be preferably, for example, the compounds shown in the columns of compounds (A) to be isomerized and isomerization products (B) of Table 1. The saccharide(s) may be one or more saccharides. The reaction mixture obtained by the above-mentioned isomerization contains an isomerization product (B), an organogermanium compound used as an isomerization agent or an isomerization accelerator, and an unreacted compound (A). The present invention can be effectively applied particularly for separation and recovery of an organogermanium compound from an aqueous solution containing the above-mentioned components, i.e. an isomerization product (B), an organogermanium compound used as an isomerization agent or an isomerization accelerator, and an unreacted compound (A).

In the present invention, the organogermanium compound to be separated and recovered is, for example, a compound represented by the above formula (2). Examples thereof can be those compounds of formula (2) wherein the $R_1$—(C)n—$R_2$ portion, the $R_3$ portion and the X portion are groups shown in Tables 2-4 given below. In these tables, the bond possessed by each group is not shown.

TABLE 2

| Compound No. | $R_1$ — (C)$_n$ — $R_2$ | $R_3$ | X |
|---|---|---|---|
| 1 | $CH_2$ | H | OH |
| 2 | $CH_3$—CH | H | OH |
| 3 | $CH_2$ | $CH_3$ | OH |
| 4 | $CH_3$—CH | $CH_3$ | OH |
| 5 | $CH_3$—C—$CH_3$ | H | OH |
| 6 | $C_6H_5$—CH | H | OH |
| 7 | $C_6H_5$—CH | $CH_3$ | OH |
| 8 | $CH_2$ | $CH_2COOH$ | OH |
| 9 | $C_6H_5$—CH | $CH_2COOH$ | OH |

TABLE 2-continued

| Compound No. | $R_1$ — (C)$_n$ — $R_2$ | $R_3$ | X |
|---|---|---|---|
| 10 | $CH_2$ | H | ONa |
| 11 | $CH_2$ | H | $NH_2$ |
| 12 | $CH_3$—CH | H | $NH_2$ |
| 13 | $CH_2$ | $CH_3$ | $NH_2$ |
| 14 | $CH_3$—CH | $CH_3$ | $NH_2$ |
| 15 | $CH_3$—C—$CH_3$ | H | $NH_2$ |

TABLE 3

| Compound No. | $R_1$ — (C)$_n$ — $R_2$ | $R_3$ | X |
|---|---|---|---|
| 16 | $C_6H_5$—CH | H | $NH_2$ |
| 17 | $C_6H_5$—CH | $CH_3$ | $NH_2$ |
| 18 | $CH_2$ | $NH_2$ | OH |
| 19 | $CH_3$—CH | $NH_2$ | OH |
| 20 | $CH_3$—C—$CH_3$ | $NH_2$ | OH |
| 21 | $CH_3$—CH | $NH_2$ | $OCH_3$ |
| 22 | $CH_3$—C—$CH_3$ | $NH_2$ | $OCH_3$ |
| 23 | $C_6H_5$—CH | $NH_2$ | OH |
| 24 | $C_6H_5$—CH | $NH_2$ | $OCH_3$ |
| 25 | $CH_2$ | $NH_2$ | $OCH_3$ |
| 26 | $CH_2$ | $NH_2$ | ONa |
| 27 | $CH_2$ | $NHCOCH_3$ | OH |
| 28 | $CH_3$—CH | $NHCOCH_3$ | OH |
| 29 | $CH_3$—C—$CH_3$ | $NHCOCH_3$ | OH |
| 30 | $CH_3$—CH | $NHCOCH_3$ | $OCH_3$ |
| 31 | $CH_3$—C—$CH_3$ | $NHCOCH_3$ | $OCH_3$ |
| 32 | $C_6H_5$—CH | $NHCOCH_3$ | OH |
| 33 | $C_6H_5$—CH | $NHCOCH_3$ | $OCH_3$ |
| 34 | $CH_2$ | $NHCOCH_3$ | $OCH_3$ |
| 35 | $CH_2$ | $NHCOCH_3$ | ONa |
| 36 | $CH_2CH_2$ | H | OH |

TABLE 4

| Compound No. | $R_1$ — (C)$_n$ — $R_2$ | $R_3$ | X |
|---|---|---|---|
| 37 | $CH_3$—CH—$CH_2$ | H | OH |
| 38 | $CH_2CH$—$CH_3$ | H | OH |
| 39 | $CH_2CH_2$ | $CH_3$ | OH |
| 40 | $C_6H_5$—$CHCH_2$ | H | OH |
| 41 | $CH_2CH_2$ | $NH_2$ | OH |
| 42 | $CH_2CH_2$ | H | $NH_2$ |
| 43 | $CH_2CH_2$ | $NHCOCH_3$ | OH |
| 44 | $CH_2CH_2CH_2$ | H | OH |
| 45 | $CH_3$—$CHCH_2CH_2$ | H | OH |
| 46 | $CH_2CH(CH_3)CH_2$ | H | OH |
| 47 | $CH_2CH_2CH_2$ | $CH_3$ | OH |
| 48 | $C_6H_5$—$CHCH_2CH_2$ | H | OH |
| 49 | $CH_2(CH_2)_2CH_2$ | H | OH |
| 50 | $CH_3CH(CH_2)_2CH_2$ | H | OH |
| 51 | $CH_2(CH_2)_3CH_2$ | H | OH |

Figure 2:
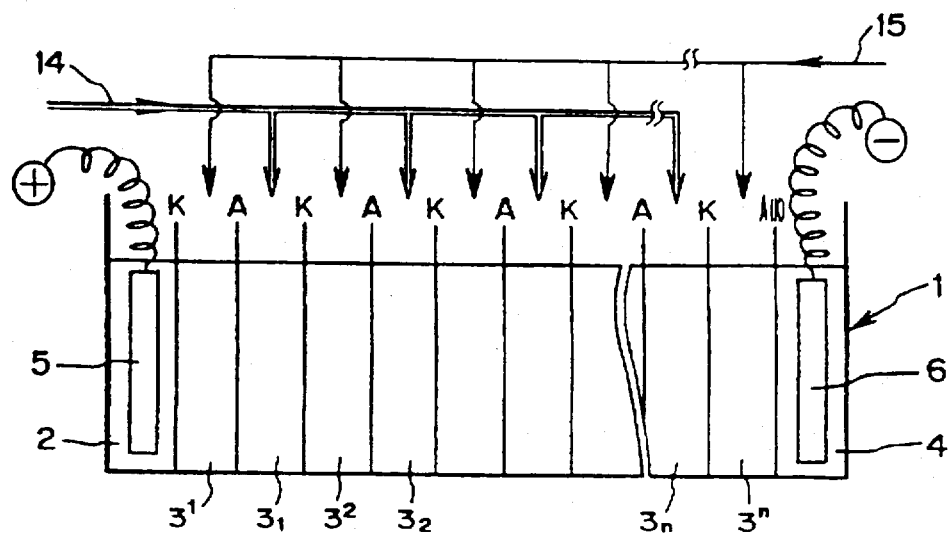
FIG. 2 is a schematic drawing showing the principle of another electrodialysis apparatus for carrying out the present invention method.

Now, description is made on the method (electrodialysis) of the present invention for separation and recovery of organogermanium compound. FIG. 1 and FIG. 2 are each a schematic drawing showing the principle of an apparatus for carrying out the present invention method.

In FIG. 1, A is an anion exchange membrane and K is a cation exchange membrane. These two ion exchange membranes A and K are provided in a container 1 so as to face each other at a given distance. They, together with the inner wall of the container 1, constitute a compartment 2, a compartment 3 and a compartment 4. The compartment 3 is a to-be-treated-solution compartment, and the compartment 2 and the compartment 4 are electrolytic solution compartments (electrode compartments) 2 and 4, respectively.

5 is an anode and 6 is a cathode. As shown in FIG. 1, the anode 5 is provided in the electrolytic solution compartment 2 defined by the anion exchange membrane A, and the cathode 6 is provided in the electrolytic solution compartment 4 defined by the cation exchange membrane K. A given voltage is applied between the electrodes 5 and 6 during an operation. Thereby, the anionic component in the to-be-treated-solution moves effectively into the compartment 2 via the anion exchange membrane A and the cationic component in the to-be-treated-solution moves into the compartment 4 via the cation exchange membrane K, and the two components are independently separated and recovered.

7 is a to-be-treated-solution tank and 8 is an electrode solution tank. The to-be-treated-solution sent from the tank 7 is fed into the to-be-treated-solution compartment 3 via a pipe 9 by a pump P; undergoes an intended dialysis treatment in the compartment 3; is returned to the tank 7 via a pipe 10; and is recirculated. Meanwhile, the electrolytic solution (e.g. aqueous sodium nitrate solution) sent from the tank 8 is fed into the electrolytic solution compartment 2 via a pipe 11 by a pump P; is subjected, in the compartment 2, to receive the components which have passed through the anion exchange membrane A; is fed into the electrolytic solution compartment 4 via a pipe 12; is returned to the tank 8 via a pipe 13; and is recirculated.

FIG. 2 is a schematic drawing showing the principle of another electrodialysis apparatus used in the present invention method. In FIG. 2, the same symbols as in FIG. 1 are used for the portions of the apparatus corresponding to those of the apparatus of FIG. 1.

In the apparatus of FIG. 2, a plurality of cation exchange membranes K and a plurality of anion exchange membranes A are provided alternately between an anode 5 and a cathode 6 so that each pair of a cation exchange membrane K and an anion exchange membrane A face each other. As also shown in FIG. 2, the apparatus contains a plurality of compartments $3X_1, 3X_2, \ldots, 3X_n$ in which each anode 5 side is defined by an anion exchange membrane A and each cathode 6 side is defined by a cation exchange membrane K (in each of these compartments is fed a to-be-treated-solution) and a plurality of compartments $3Y_1, 3Y_2, \ldots, 3Y_n$ in which each anode 5 side is defined by a cation ion exchange membrane K and each cathode 6 side is defined by an anion exchange membrane A. The compartments $3X_1, 3X_2, \ldots, 3X_n$ and the compartments and $3Y_1, 3Y_2, \ldots, 3Y_n$ are provided alternately. In FIG. 2, 14 is a pipe for feeding a to-be-treated-solution and 15 is a pipe for feeding an electrolytic solution.

The above is the basic constitution of the apparatus of FIG. 2 (when the number of the compartments $3X_1, 3X_2, \ldots, 3X_n$ and $3Y_1, 3Y_2, \ldots, 3Y_n$ is one, the number of the total compartments is three and the apparatus is the same as one shown in FIG. 1). The apparatus of FIG. 2 can be any of a filter press type or a unit cell type (a water tank type) as long as the apparatus has the above basic constitution. Each of the anion and cation exchange membranes can be a homogeneous type or a heterogeneous type, or a condensate type or a polymer type (this applies also to the apparatus of FIG. 1). In FIG. 2, none of the pipe for discharging the to-be-treated-solution and the pipe for discharging the electrode solution is shown, but these pipes are provided in the same manner as in FIG. 1 and any of batch type and circulation type can be employed as necessary.

In operating the apparatus of FIG. 2, a to-be-treated-solution of the present invention, i.e. a mixed solution containing a saccharide(s) and an organogermanium compound is fed into the compartments $3X_1, 3X_2, \ldots, 3X_n$ via the pipe 14. Water or an aqueous solution containing an appropriate electrolyte (e.g. an aqueous sodium nitrate solution) is fed into the compartments $3Y_1, 3Y_2, \ldots, 3Y_n$ via the pipe 15. An appropriate solution is used as an electrolyte solution for the electrode compartments 5 and 6. This solution may be any solution capable of passing electricity therethrough and may be the same as the aqueous solution fed into the compartments $3Y_1, 3Y_2, \ldots, 3Y_n$.

The voltage applied to the dialysis apparatus during the operation of the apparatus is preferably about 0.1–1.0 V per anion or cation exchange membrane unit, and the current density is preferably about 1–20 A/dm². The voltage and the current density are not restricted thereto and can be determined appropriately depending upon, for example, the kinds and concentrations of saccharide(s) and organogermanium compound contained in a to-be-treated-solution and the scale of electrodialysis apparatus used.

By the above operation, the cations in the to-be-treated-solution pass through the cation exchange membranes K and the anions in the to-be-treated-solution pass through the anion exchange membranes A; as a result, the cations and the anions move from a plurality of the compartments $3X_1, 3X_2, \ldots, 3X_n$ each defined by an anion exchange membrane A and a cation exchange membrane K, toward the electrodes having opposite charges into the compartments $3Y_1, 3Y_2, \ldots, 3Y_n$, and separation is conducted. In the to-be-treated-solution compartments $3X_1, 3X_2, \ldots, 3X_n$ remain substances having no charge, and separation is conducted.

In the present invention, it has been made clear for the first time that organogermanium compounds are electrolytes each consisting of a cation and an anion capable of passing through a cation exchange membrane and an anion exchange membrane, respectively. Thus, by feeding a mixed solution containing a saccharide(s) and an organogermanium compound, into the to-be-treated-solution compartments $3X_1, 3X_2, \ldots, 3X_n$, and conducting the above-mentioned electrodialysis operation continuously, the anions and the cations both constituting the organogermanium compound are moved, through the cation exchange membranes and the anion exchange membranes, respectively, from the to-be-treated-solution compartments $3X_1, 3X_2, \ldots, 3X_n$ to the electrolytic solution compartments $3Y_1, 3Y_2, \ldots, 3Y_n$ and can be separated and recovered. Although the details of the charge state of the compound having the formula (2) are unknown, the compound can be separated and recovered very effectively from saccharide(s) by the present invention method.

EXAMPLES

The present invention is hereinafter described by way of Examples. Needless to say, however, the present invention is not restricted to the Examples.

In each of the present Examples, there was conducted, as follows, a test for separating and recovering an organogermanium compound from a mixed solution containing a saccharide(s) and said organogermanium compound (2-carboxyethylgermanium sesquioxide was used as a typical example), used or isomerized in an isomerization reaction. In each test, there was used, as a test apparatus, an electrodialysis apparatus having a constitution as shown in. FIG. 1.

<Example 1>

There was prepared, as an electrodialysis apparatus, a three compartment type electrodialysis cell, Selemion DU-Ob (tradename, product of Asahi Glass Co., Ltd., effective membrane area=2.09 dm²/pair); and storage tanks and pipes were connected thereto as shown in FIG. 1. As pump P, there were provided two independent pumps, one for circulation of a solution to be treated and the other for circulation of an electrode solution. There were used, as a cation exchange membrane K, Selemion CMV (trade name, strongly acidic cation exchange membrane, product of Asahi Glass Co., Ltd.) and, as an anion exchange membrane A, Selemion AMV (trade name, strongly basic anion exchange membrane, product of Asahi Glass Co., Ltd.).

solution, fructose (Example 2), a glucose/fructose mixture (Example 3), lactose (Example 4), lactulose (Example 5) and a lactose/lactulose mixture (Example 6), whereby reduction ratios after 15 minutes desalting or 30 minutes desalting were determined. The results are also shown in Table 5.

TABLE 5

| Example No. | Desalting time Components in mixed solution | 0 min Concentration before desalting $C_1$ (mM) | 15 min Concentration after desalting $C_2$ (mM) | 15 min Reduction $C_1-C_2$ | 15 min Reduction rate (%) | 30 min Concentration after desalting $C_2$ (mM) | 30 min Reduction $C_1-C_2$ | 30 min Reduction rate (%) |
|---|---|---|---|---|---|---|---|---|
| Example 1 | Glucose (mM) | 10.1 | 9.915 | 0.185 | 1.83 | 9.095 | 0.195 | 1.93 |
|  | Ge-132 (mM) | 4.15 | 0.963 | 3.187 | 76.80 | 0.1615 | 3.9885 | 96.11 |
| Example 2 | Fructose (mM) | 10.3 | 9.13 | 1.17 | 11.36 | 9.1 | 1.2 | 11.65 |
|  | Ge-132 (mM) | 4.17 | 0.68 | 3.49 | 83.69 | 0.1105 | 4.0595 | 97.35 |
| Example 3 | Glucose (mM) | 10.1 | 9.65 | 0.45 | 4.46 | 9.7 | 0.405 | 4.01 |
|  | Fructose (mM) | 9.71 | 9.105 | 0.605 | 6.23 | 9.11 | 0.61 | 6.18 |
|  | Ge-132 (mM) | 4.03 | 1.36 | 2.67 | 66.25 | 0.39 | 3.64 | 90.35 |
| Example 4 | Lactose (mM) | 9.94 | 9.865 | 0.075 | 0.75 | 9.925 | 0.015 | 0.15 |
|  | Ge-132 (mM) | 4.16 | 1.15 | 3.01 | 72.36 | 0.167 | 3.993 | 95.99 |
| Example 5 | Lactulose (mM) | 9.81 | 9.575 | 0.235 | 2.40 | 9.635 | 0.715 | 1.78 |
|  | Ge-132 (mM) | 4.2 | 0.914 | 3.286 | 78.24 | 0.191 | 4.009 | 95.45 |
| Example 6 | Lactose (mM) | 9.79 | 9.71 | 0.08 | — | 9.585 | 0.205 | — |
|  | Lactulose (mM) | 9.88 | 9.61 | 0.27 | 2.73 | 9.72 | 0.16 | 1.62 |
|  | Ge-132 (mM) | 4.18 | 1.23 | 2.95 | 70.57 | 0.326 | 3.854 | 92.20 |

An operation was conducted as follows. As shown in FIG. 1, a to-be-treated-solution in a storage tank 7 therefor was introduced, by a pump P, into a to-be-treated-solution compartment 3 wherein an anion exchange membrane A and a cation exchange membrane K were provided, and circulated. An electrode solution (0.5 N aqueous sodium nitrate solution) was introduced into electrode compartments 2 and 4 and circulated. In this state, an electric current was passed between a cathode and an anode, under the conditions of a voltage of 0.2 V per anion or cation exchange membrane unit and a current density of 8 A/dm². The introduction rates and circulation rates of the to-be-treated-solution and the electrode solution were both 2 cm/sec in terms of linear speed at membrane surface.

In this Example 1, there was used, as a sample solution, a solution containing glucose as a saccharose in a concentration of 10.1 mM/l and 2-carboxyethylgermanium sesquioxide (hereinafter abbreviated to Ge-132) as an organogermanium compound in a concentration of 4.15 mM/l. About 10 ml of the sample solution was placed in the storage tank 7, introduced into the compartment 3 by the pump P, and circulated. 50 ml of a 0.5 N sodium nitrate solution was used as the electrode solution, and was introduced and circulated as shown in FIG. 1. An operation was conducted for 15 minutes or 30 minutes to conduct a desalting treatment.

Then, the sample solution recovered in the tank 7 and the electrode solution recovered in the tank 8 were each measured for glucose concentration and Ge-132 concentration to determine respective reduction ratios after 15 minutes or 30 minutes. Incidentally, glucose concentration was measured by the calibration curve method of high-performance liquid chromatography, and Ge-132 concentration was measured by the standard addition method of flame atomic spectroscopy. The results are shown in Table 5.

<Examples 2–6>

The procedure of Example 1 was repeated except that there were used, as the saccharide component in the mixed As is clear from the results of Examples 1–6, the present invention method allows for very effective separation and recovery of organogermanium compound. In Example 1, for example, the reduction ratio of Ge-132 after 15 minutes is 76.80% (the compound moved into the electrode solution and was recovered by that much), and that after 30 minutes is as high as 96.11%. Similar tendencies are seen in Examples 2–6. Thus, the effect of separation and recovery is excellent.

<Example 7>

Application of present method to isomerization mixture after glucose isomerization into fructose A Ge-132 solution (75 mM/l) was added to a glucose solution (150 mM/l). The mixture was adjusted to pH 9.03 with sodium hydroxide and subjected to isomerization (glucose into fructose) with shaking at 80° C. Three hours later, the amount of formed fructose and the amount of remaining glucose were determined using a high-performance liquid chromatograph (Shimadzu 7A). As a result, the isomerization ratio of glucose into fructose was as high as 98.9%. The concentrations of glucose, fructose and Ge-132 in the isomerization mixture were 1.65 mM/l, 148 mM/l and 75 mM/l, respectively. The mixture was diluted ten-fold and then measured for reduction ratios after 15 minutes electrodialysis or 30 minutes electrodialysis, in the same manner as in Example 1. The results are shown in Table 6.

TABLE 6

| | | 0 min | 15 min | | | 30 min | | |
|---|---|---|---|---|---|---|---|---|
| Example No. | Desalting time Components in mixed solution | Concentration before desalting $C_1$ (mM) | Concentration after desalting $C_2$ (mM) | Reduction $C_1-C_2$ | Reduction rate (%) | Concentration after desalting $C_2$ (mM) | Reduction $C_1-C_2$ | Reduction rate (%) |
| Example 7 | Glucose (mM) | 0.165 | 0.154 | 0.011 | 7.14 | 0.154 | 0.011 | 6.67 |
| | Fructose (mM) | 14.8 | 13.26 | 1.54 | 10.41 | 13.22 | 1.58 | 10.67 |
| | Ge-132 (mM) | 7.5 | 1.38 | 6.12 | 81.56 | 0.36 | 7.14 | 96.25 |

Industrial Applicability

As stated above, the present invention method allows for very effective separation and recovery of an organogermanium compound from a mixed solution containing a saccharide(s) and said organogermanium compound, by a separation method using ion exchange membranes. Further, the present invention method is particularly effective for separation and recovery of an organogermanium compound from a reaction mixture obtained when a compound having an aldose structure is isomerized into a compound having a ketose structure by using said organogermanium compound as an isomerization agent or an isomerization accelerator.

We claim:

1. A method for separating and recovering an organogermanium compound from a mixed solution containing a saccharide or saccharides and said organogermanium compound, which method comprises passing an electric current through a mixed solution containing a saccharide or saccharides and an organogermanium compound, in one or more compartments each defined by one pair of an ion exchange membrane and a cation exchange membrane facing each other, whose anode side is defined by an anion exchange membrane and whose cathode side is defined by a cation exchange membrane, to separate and recover said organogermanium compound from said mixed solution.

2. A method of claim 1 for separating and recovering an organogermanium compound from a mixed solution containing a saccharide or saccharides and said organogermanium compound, wherein the organogermanium is an organogermanium compound represented by the following formula (2):

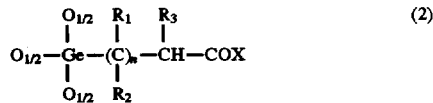

wherein $R_1$, $R_2$ and $R_3$ may be the same or different and are each independently a hydrogen atom, a lower alkyl group, a carboxyalkyl group, a substituted or unsubstituted phenyl group or an amino group which may be protected by an appropriate protective group; X is a hydroxyl group, an O-lower alkyl group, an amino group or a salt represented by OY, wherein Y is a metal or a basic compound; and n is an integer of 1 or more.

3. A method of claim 2 for separating and recovering an organogermanium compound from a mixed solution containing a saccharide or saccharides and said organogermanium compound, wherein the mixed solution is a mixed solution containing a saccharides mixture and an organogermanium compound, obtained when a compound having an aldose structure is isomerized into a compound having a ketose structure in the presence of said organogermanium compound and an isomerase.

4. A method of claim 2 for separating and recovering an organogermanium compound from a mixed solution containing a saccharide or saccharides and said organogermanium compound, wherein the mixed solution is a mixed solution containing a saccharides mixture and an organogermanium compound, obtained when a compound having an aldose structure is isomerized into a compound having a ketose structure in the presence of said organogermanium compound.

5. A method of claim 1 for separating and recovering an organogermanium compound from a mixed solution containing a saccharide or saccharides and said organogermanium compound, wherein the mixed solution is a mixed solution containing a saccharides mixture and an organogermanium compound, obtained when a compound having an aldose structure is isomerized into a compound having a ketose structure in the presence of said organogermanium compound.

6. A method of claim 5 for separating and recovering an organogermanium compound from a mixed solution containing a saccharide or saccharides and said organogermanium compound, wherein the mixed solution is a mixed solution containing a saccharides mixture and an organogermanium compound, obtained when a compound having an aldose structure is isomerized into a compound having a ketose structure in the presence of said organogermanium compound and an isomerase.

7. A method of claim 1 for separating and recovering an organogermanium compound from a mixed solution containing a saccharide or saccharides and said organogermanium compound, wherein the mixed solution is a mixed solution containing a saccharides mixture and an organogermanium compound, obtained when a compound having an aldose structure is isomerized into a compound having a ketose structure in the presence of said organogermanium compound and an isomerase.

* * * * *